United States Patent [19]

Askin et al.

[11] Patent Number: 4,920,218

[45] Date of Patent: Apr. 24, 1990

[54] NOVEL HYDROXIDE MEDIATED FK-506 REARRANGEMENT PROCESS

[75] Inventors: David Askin; Todd K. Jones, both of Edison; Robert A. Reamer, Bloomfield; Ralph P. Volante, East Windsor; Ichiro Shinkai, Westfield, all of N.J.

[73] Assignee: Merck & Co., Inc., Rahway, N.J.

[21] Appl. No.: 403,794

[22] Filed: Sep. 5, 1989

Related U.S. Application Data

[63] Continuation of Ser. No. 256,784, Oct. 12, 1988, abandoned.

[51] Int. Cl.⁵ .................. C07D 498/16; C07D 498/18

[52] U.S. Cl. ...................................... 540/456; 540/452
[58] Field of Search ................................. 540/455, 456

[56] References Cited

FOREIGN PATENT DOCUMENTS 63-17884  6/1988  Japan .................................... 540/456

Primary Examiner—Robert T. Bond
Attorney, Agent, or Firm—Melvin Winokur; Joseph F. Diprima

[57] ABSTRACT

A process is described involving an alkaline rearrangement of FK-506 producing a new decarbonylated 22-membered macrocycle rearrangement derivative of FK-506, i.e. C.9, nor-keto FK-506.

10 Claims, No Drawings

NOVEL HYDROXIDE MEDIATED FK-506 REARRANGEMENT PROCESS

This is a continuation, of application Ser. No. 256,784, filed Oct. 12, 1988, now abandoned.

BACKGROUND OF THE INVENTION

1. Field of the Invention

This invention relates to a process for producing a C.9 nor-keto FK-506 hydroxide mediated rearrangement product, which is an intermediate for producing an immunosuppressant.

2. Brief Description of Disclosures in the Art

In 1983, the US FDA licensed cyclosporin, an extremely effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication No. 0184162 to Fujisawa, hereby incorporated by reference, describes a new macrolide immunosuppressant FK-506 which is reputed to be 100 times more effective than cyclosporin. The macrolide is produced by fermentation of a particular strain of *Streptomyces tsukubaensis* No. 9993 (FERM BP-927). Also described are the closely related macrolide immunosuppressants FK-525, produced by the same microorganism, and FK-520 and FK-523, produced by *S. hygroscopicus* subsp. *yakushimaensis*.

The novel 23-membered tricyclo-macrolide FK-506 was isolated and characterized by Tanaka, Kuroda, and co-workers, see JACS, 109, pp. 5031, 1987, and EPO Publication No. 0184162. The potential usefulness of such an agent in bone marrow and organ transplantations coupled with its unique structural features has prompted many in the field to initiate efforts towards the synthesis of FK-506 type macrolide structures, by contacting FK-506, with different chemical reagents under a variety of conditions to produce molecular modifications thereof, some of which may exhibit greater immunosuppressant activity than the naturally occurring form itself.

For example, Tanaka et al (Fujisawa) have reported in *J. Am. Chem. Soc.*, 1987, 108, p. 5031, that alkaline treatment of FK-506 (1) leads to the hydrolysis product 6 assigned structure shown below, which is not described as having immunosuppressant properties.

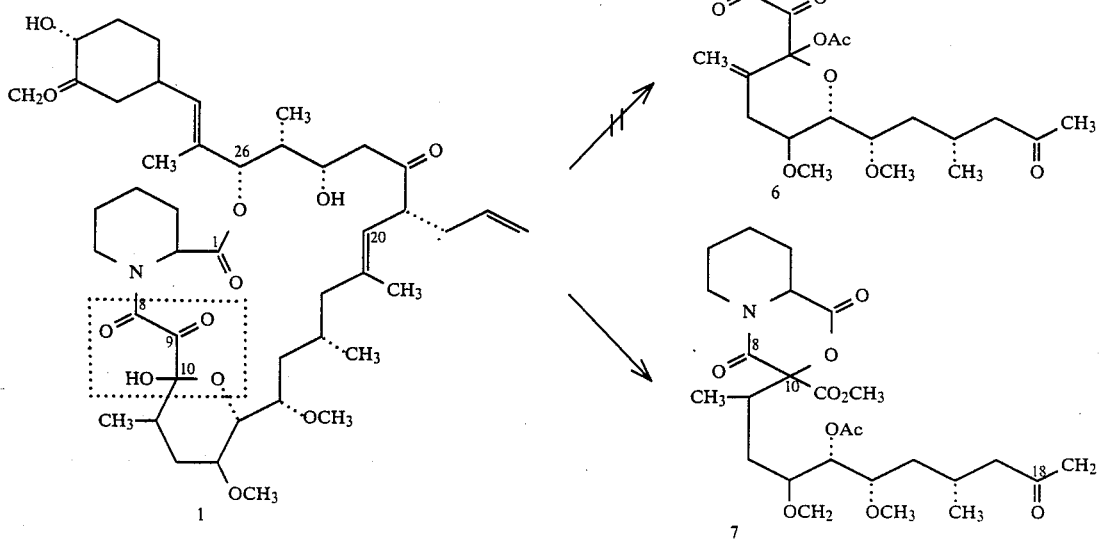

There is a continuing search for new and more therapeutically effective molecular modifications of FK-506 having diminished adverse and toxic side effects. See for example: (a) Askin, D.; Volante, R. P.; Reamer, R. A.; Ryan, K. M.; Shinkai, I. *Tetrahedron Lett.*, 1988, 29, p. 277; (b) Mills, S.; Desmond, R.; Reamer, R. A.; Volante, R. P.; Shinkai, I. *Tetrahedron Lett.*, 1988, 29, p. 281; (c) Desmond, R.; Mills, S. G.; Volante, R. P.; Shinkai I. *Tetrahedron Lett.*, 1988, 29, p. 3895; (d) Askin, D.; Volante, R. P.; Ryan, K. M.; Reamer, R. A.; Shinkai, I. *Tetrahedron Lett.*, 1988, 29, p. 4245.

SUMMARY OF THE INVENTION

It has been unexpectedly found that the above-illustrated alkaline treatment of the L-679,934 (FK-506) C.8-C.10 tricarbonyl functional group array leads not to the formerly assigned structure 6, but rather to the assigned structure 7, (after esterification, acetylation and ozonolysis) as shown.

Furthermore, the C.24, C.32-Bis-protected form of FK-506 (2) undergoes the same rapid cleavage of the C.8-C.9 bond with concomitant formation of the alpha-hydroxy acid 3, containing a new carbon bond between C.8 and C.10 in the presence of 1.0 equivalent of hydroxide ion (benzilic acid type rearrangement). Unexpectedly, no cleavage of the C.26 pipecolinic ester linkage is observed under these mild reaction conditions.

Lead tetraacetate oxidative decarboxylation of the newly formed alpha-hydroxy acid 3 gives the novel nor-C.9 keto-FK-506 analog (22-membered macrolide) 4, which is deprotected to yield the new immunosuppressant 5.

In accordance with this invention there is provided: a process comprising the steps of:

(a) contacting compound 2:

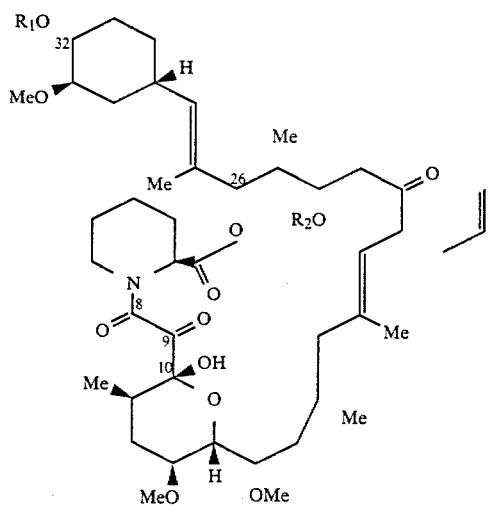

wherein $R_1$ and $R_2$ are independently H, or an easily removable hydroxy protecting group, with a hydroxide base in an inert aqueous/organic solvent mixture at room temperature in the range of about 0°–25° C. for a sufficient time to form 3;

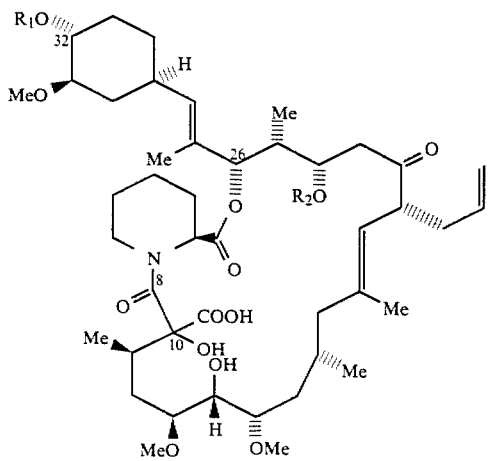

(b) contacting 3 obtained above with an oxidizing agent in an inert organic solvent at 0°–25° C. for a sufficient time to form 4;

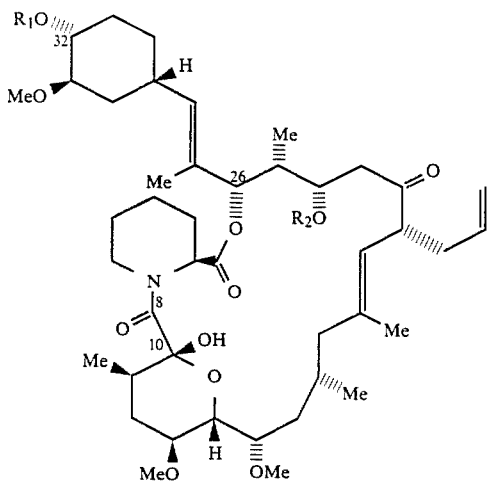

(c) contacting the above-obtained 4 under mild acidic hydrolysis conditions for a sufficient time to remove $R_2$, and $R_1$ if present, to yield the immunosuppressant 5:

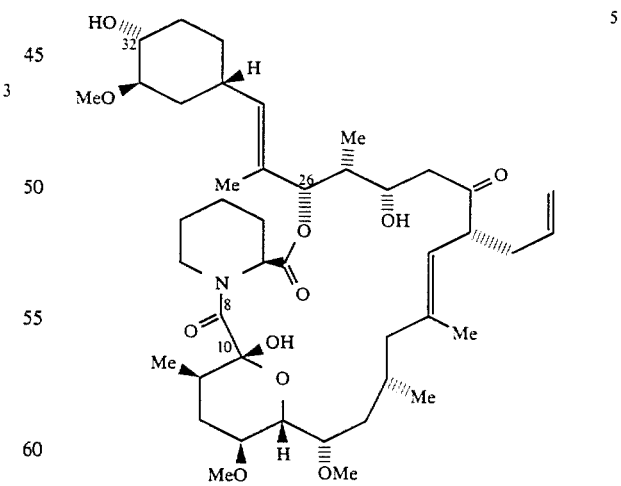

In addition, there is provided a compound of the structure:

5

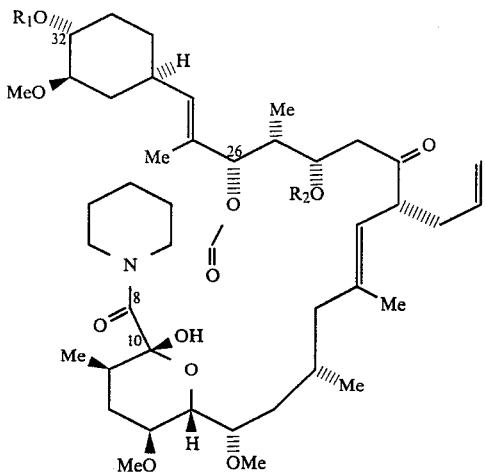

6 wherein $R_1$ and $R_2$ are independently H, or an easily removable hydroxy protecting group.

BRIEF DESCRIPTION OF THE INVENTION AND PREFERRED EMBODIMENTS

The process described herein is a mild and selective procedure for the conversion of FK-506 or similar macrolide tricarbonyl containing derivatives to their corresponding nor-keto hemiketal derivatives. This novel methodology provides access to a variety of interesting and potentially biologically active FK-506 derivative compounds, which are not available by existing methodology.

The invention can be easily understood by reference to the following reaction scheme diagram:

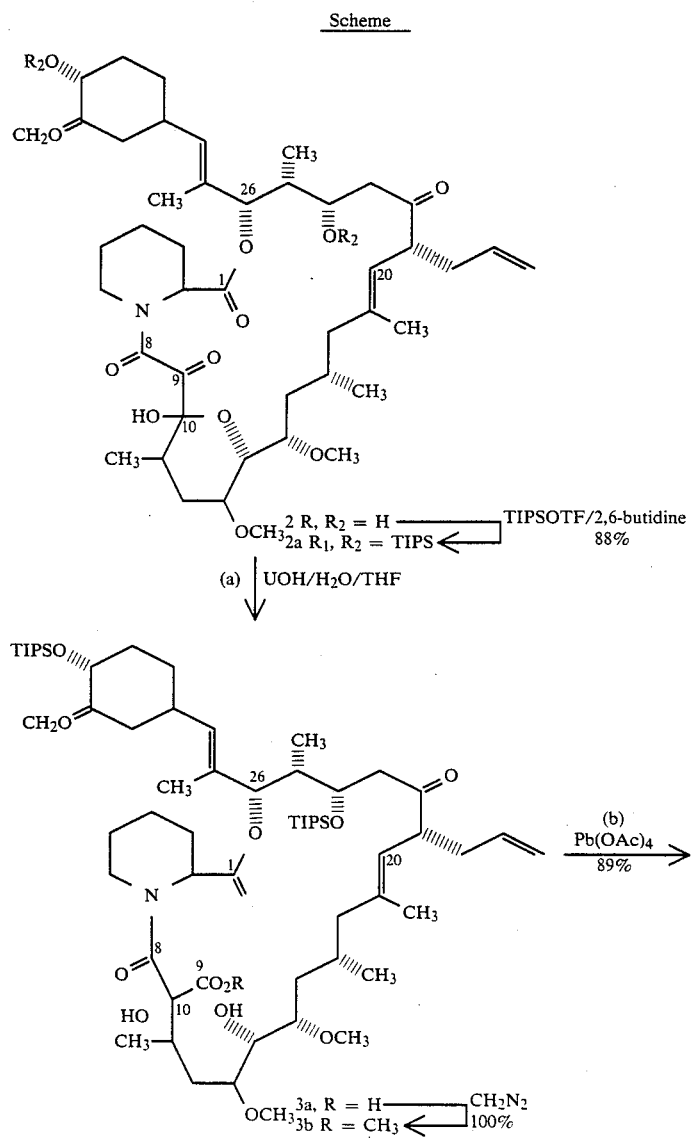

-continued

Scheme

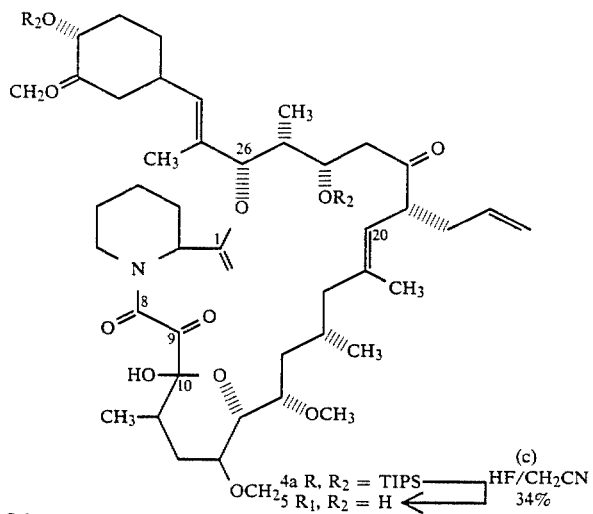

4a R, R$_2$ = TIPS ⟶ HF/CH$_2$CN (c)
5 R$_1$, R$_2$ = H ⟵ 34%

Scheme

The first step, (a), involves the alkaline mediated benzilic acid rearrangement of 2, where R$_1$ is H, or an easily removable protecting group, which can be conventional in the art, e.g. Si(R)$_3$ where R is independently C$_1$-C$_4$ linear or branched alkyl, phenyl, or benzyl, and where (R)$_3$ can be trimethyl, triethyl, triisopropyl, dimethyl-t-butyl, dimethyl isopropyl, diphenyl t-butyl, triphenyl, tribenzyl; R$_1$ can also be C$_1$-C$_{10}$ acyl, e.g. acetyl, or halogenated C$_1$-C$_{10}$ acyl, e.g. trifluoroacetyl, trichloroacetyl, or C$_1$-C$_{10}$ halogenated alkyl, that can be readily removed by conventional methods in the art, e.g. mild acid hydrolysis conditions (e.g. 48% HF in acetonitrile at 25° C.), for example, —CH$_2$—CCl$_3$. A preferred protecting group is triisopropylsilyl (TIPS).

R$_2$ may be the same or different from R$_1$ and is independently chosen from the same list of radicals as described above for R$_1$. Preferably R$_2$ is a protecting group, being other than H in the process, and particularly preferred is where both R$_1$ and R$_2$ are the same protecting groups. Steps (a), (b) and (c) are carried out much more efficiently, in higher yield, less by-products, and less required purification, both R$_1$ and R$_2$, are protected.

The preparation of starting material 2 is conducted by conventionally treating FK-506, which process is described in Fujisawa's EPO Publication No. 0184162, hereby incorporated by reference for this particular purpose, with 2 to 4 equivalents of an activated protecting agent to form R$_1$ and/or R$_2$, as defined above, such as acetyl chloride, trifluoroacetyl chloride, or a silylating agent such as the corresponding trialkyl silyl chloride, silyl triflate, or trifluoromethanesulfonate, e.g. dimethyl-t-butyl chloride, tribenzyl triflate or triisopropylsilyl trifluoromethanesulfonate, and the like, in the presence of an amine base such as 2,6-lutidine, imidazole, or 2,6-di-t-butyl pyridine, and the like, in an anhydrous, inert organic solvent, e.g. C$_2$-C$_{10}$ acyclic or cyclic ethers, such as diethylether, dioxane, tetrahydrofuran; chlorinated C$_1$-C$_4$ alkanes, e.g. methylene chloride, C$_6$-C$_{10}$ aromatic hydrocarbons, e.g. benzene, toluene, and the like, at −50° to 25° C., preferably at 25° C., for sufficient time to effect protection of the C.24 and C.32 hydroxyl functions.

Preferably 2–4 equivalents of protecting agent per equivalent of FK-506 is used.

Yields of the protection reaction are essentially quantitative.

Step (a) of said process (hydroxide mediated benzilic acid rearrangement) is effected by treating 2 with 1–10 equivalents, of a hydroxide base M(OH)$_n$ where M is Na, K, Cs, Li, Mg, Ca, Ba, or other monovalent or divalent metallic counterion species, where n is 1 or 2. Preferred is lithium hydroxide as the alkaline reagent and a preferred amount of base used is 3–10% molar excess of alkaline agent to 2, i.e. 1.03–1.10 equivalents/per equivalent of 2.

The reaction is carried out in a mixture of water and an organic co-solvent that is partially soluble or miscible with water. The organic solvents operable in the invention include C$_1$-C$_{10}$ cyclic and acyclic organic ethers, same as described above, e.g. diethyl ether, dioxane, tetrahydrofuran, and C$_1$-C$_4$ alkyl nitriles, e.g. acetonitrile, and the like. Preferred solvent system is tetrahydrofuran/water. The volume ratio of water/organic co-solvent is about 1:5, preferably 1:5 and the amount of water/organic co-solvent mixture used per weight of 2 is about 16 mL vol./1 g wt. of 2. Said reaction is carried out at 0°–25° C. preferably 0°–5° C., for sufficient time to selectively afford 3. The isolation is generally conducted by acidification with a mineral acid, e.g. HCl, followed by extraction with a water-immiscible organic solvent, e.g. ethyl acetate. Purification is conventional and can be carried out by HPLC.

Yields are nearly quantitative, being 95%+.

Step (b) of the instant invention process is carried out by contacting the hydroxy acid 3 with an oxidizing agent such as an alkali metaperiodate, e.g. sodium metaperiodate, and the like, or lead tetraacetate in dry organic solvent including C$_6$-C$_8$ aromatic hydrocarbons, C$_6$-C$_8$ linear or branched acyclic or cyclic paraffins, e.g. benzene, hexane, toluene, m-xylene, cyclohexane, and the like, preferably benzene, at 0°–50° C., preferably 20°–25° C., for a sufficient amount of time to effect oxidative cleavage to the desired nor-keto hemiketal 4. (The ester 3b as shown can be used for spectral identification purposes, but is not used in the oxidative decarboxylation.)

The amount of oxidizing agent, preferably being lead tetraacetate, used is 1:1 equivalents of oxidizing agent/equivalent of 3, and preferably 1:1 equivalents/eq. 3.

The amount of solvent used is 28 mL volumes per 1 g weight of 3.

Isolation and purification are conventional and usually involve organic solvent extraction and chromatography.

Yields in this process steps are high and in the range of 95%+.

Step (c) of the process, involving removal of the protecting groups, e.g. silyl-protecting groups, is conventional and carried out by treating, e.g. the bis-silyl nor-keto hemiketal 4, under mild acidic hydrolysis conditions, with an acid such as trifluoroacetic acid or 48% aqueous HF, in an organic solvent, including $C_2-C_{10}$ cyclic and acyclic ethers, $C_1-C_4$ alkylnitriles, $C_6-C_8$ aromatic hydrocarbons, e.g. acetonitrile, tetrahydrofuran, diethylether, benzene, toluene, and the like, at 0°–25° C., preferably 20°–25° C., for a time sufficient to effect hydrolysis of the protecting groups, e.g. silyl groups, to afford the desired hemiketal 5.

Isolation and purification of 5 are conventional in the art. Yields are almost quantitative, 95%+.

The material 5 of the present invention possesses pharmacological activity such as immunosuppressive activity, antimicrobial activity, and the like, and therefore is useful for the treatment and prevention of the transplantation rejection of organs or tissues such as heart, kidney, liver, medulla ossium, skin, etc., graft-versus-host diseases by medulla ossium transplantation, auto-immune diseases such as rheumatoid arthritis, systemic lupus erythematosus, Hashimoto's thyroiditis, multiple sclerosis, myasthenia gravis, type I diabetes, uveitis, and the like.

The pharmaceutical composition of this invention can be used in the form of a pharmaceutical preparation, for example, in solid, semisolid or liquid form, which contains 5, of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

For applying this composition to a human, it is preferable to apply it by parenteral or enteral administration. While the dosage of therapeutically effective amount of 5 varies from, and also depends upon the age and condition of each individual patient to be treated, a daily dose (calculated on the basis of a 70 kg man) of about 0.01–1000 mg, preferably 0.1–500 mg and more preferably 0.5–100 mg, of the active ingredient is generally given for treating diseases, and an average single dose of about 0.5 mg, 1 mg, 5 mg, 10 mg, 50 mg, 100 mg, 250 mg and 500 mg is generally administered.

The following examples are illustrative of the invention as conceived by us and should not be construed as being limitations on the scope and spirit of the instant invention.

EXAMPLE 1

Preparation of Bis-Triisopropylsilyloxy FK-506 (2a)

FK-506 1 (1.00 g, 1.245 mmol as described in Fujisawa's EPO Publication No. 0184162) was dissolved in 12 ml of methylene chloride and cooled to 0° C. under a nitrogen atmosphere. 2,6-Lutidine (5.0 equiv., 726 microliters) and triisopropylsilyl triflate (1.4 mL, 4.2 equiv.) were added successively at 0° C. The solution was warmed to 25° C. over 2 hours and then allowed to stir at 25° C. for 2-3 days. The mixture was assayed for completeness of reaction by TLC (2:1 hexanes:ethyl acetate). The reaction was quenched by the addition of 3.0 equivalents of methanol (151 microliters) and aged for 15 minutes at 25° C. The mixture was then partitioned between 25 ml of saturated sodium bicarbonate solution and 50 ml of methylene chloride. The aqueous layer was further extracted with 2×50 ml of methylene chloride. The organic layers were combined and washed with 25 ml of water, dried over magnesium sulfate, and concentrated in vacuo to an oil. The crude product was flash chromatographed over 100 g of silica gel (eluting with hexanes:ethyl acetate, 5:1) to give the bis-TIPS FK-506 (2a) as a white foam (1.36 g, 97.8% yield). The material was homogeneous by proton NMR.

EXAMPLE 2

LiOH FK-506 Cleavage Product 3a

C.24, C.32-Bis-TIPS-FK-506 (2a) (631.6 mg, 0.566 mmol) was dissolved in 10 ml (5:1) tetrahydrofuran/water and cooled to 0° C. Solid lithium hydroxide monohydrate (24.3 mg, 1.03 equiv.) was added and the mixture was stirred at 0°–4° C. for 1 hour and warmed to +25° C. and aged 5–13 hr (TLC analysis at this time indicated complete consumption of starting material, hexanes:ethyl acetate, 2:1). The reaction mixture was diluted with 30 ml of water, 290 microliters of 2N HCl was added, and the solution was extracted with 3×50 ml portions of ethyl acetate. The organic layers were combined, washed with 25 ml of water, 25 ml of saturated sodium chloride solution, and dried over magnesium sulfate. Concentration in vacuo gave the hydroxy acid rearranged FK-506 product 3a as a white foam (659.4 mg, 102.7% mass recovery) ir (CHCl$_3$) 3600(s), 3500–3000(b), 1770, 1730, 1710, 1630 cm$^{-1}$.

EXAMPLE 3

Nor-C.9-Keto Bis-TIPS FK-506 4a

Hydroxy acid 3a (72.4 mg, 0.0639 mmol) was dissolved in 2 ml of dry benzene at 20°–24° C. and 28.5 mg of lead tetraacetate was added (0.0643 mmol). The mixture was aged at 20°–24° C. for 1 hr (TLC analysis at this time showed the absence of starting material, hexanes:ethyl acetate, 5:1). The mixture was quenched with 5 ml of saturated sodium bicarbonate solution and extracted with 2×75 ml of methylene chloride. The methylene chloride fractions were combined, washed with 25 ml of water, and dried over magnesium sulfate. Concentration in vacuo gave 76.4 mg of an oil. The crude oil was purified by flash chromatography over silica gel (elution with hexanes:ethyl acetate 6:1) to give 66.2 mg of the desired nor-C.9 keto product 4a as an oil (95.3%), ir (CHCl$_3$) 1735, 1710, 1635 cm$^{-1}$.

EXAMPLE 4

C.9-Nor-Keto FK-506 (5)

Bis-TIPS-nor-C.9-keto FK-506 (4a) (80.4 mg) was dissolved in 3.0 ml of acetonitrile at 24°-25° C. Eight drops of 50% hydrofluoric acid was added and the mixture was stirred at 24°-25° C. for 1 hr (TLC at this time showed the absence of starting material; however, there appeared to be a mixture of non silylated and mono-silylated products present, 3:1, hexanes:ethyl acetate). The mixture was aged for 5 hr at 24°-25° C., quenched by the addition of 5 ml of saturated sodium bicarbonate solution, and extracted with 3×50 ml of ethyl acetate. The combined organic extracts were washed with 25 ml of saturated sodium chloride solution, dried over sodium sulfate, and concentrated in vacuo to give 63.2 mg of an oil. The oil was purified by flash chromatography over silica gel (elution with hexanes:ethyl acetate, 1:3 to 100% ethyl acetate) to give 19.5 mg of nor-C.9-keto FK-506 (5), mass spectrum: calculated for C$_{43}$H$_{69}$NO$_{11}$: 775.487065. Found: 775.4868.

CORRELATION OR NMR SPECTRA AND STRUCTURAL ASSIGNMENTS

The presence of a carboxylic acid in 3a (see note 1) was verified by isolation of ester 3b upon treatment with diazomethane. Comparison of the $^{13}$C NMR spectrum of the acid 3a with FK-506 and related compounds (vide infra) revealed that a rearrangement of the tricarbonyl linkage had occurred. The characteristic resonance of C$_9$ (see Table) at 196 ppm (major rotamer of 1 and 2a) was absent and a new carbonyl resonance appeared at 173.1 ppm (only observed signal assignable to C$_9$). Additionally, the C$_{10}$ resonance at 97 ppm (major rotamer of 1 and 2a) was shifted upfield to 82.4 ppm. These observations, along with the reported tendency of vicinal polyketones to undergo a facile hydroxide induced 1,2-acyl migration, (see notes 2, 3) led us to interpret these new signals as arising from formation of an acid carbonyl from C$_9$ and concomitant opening of the lactol ring (shifting the C$_{10}$ resonance upfield) as shown in 3a, rather than the predicted open-chain hydroxy-acid. Furthermore, oxidation of 3a with lead tetraacetate (see note 4) (1.0 equiv., benzene, 25° C.) resulted in clean decarboxylation to produce bis-TIPS ether 4a in 95% yield. Desilylation (95:5 CH$_3$CN:48% aqueous HF, 25° C.) (see note 5) then afforded des-C$_9$-KF-506, 5.

TABLE

Selected $^{13}$C NMR Chemical Shift Data for FK-506 and Related Compounds Carbon 13 Chemical Shifts for the C$_3$-C$_{10}$ Portion of FK-506 and Related Compounds (Major, Minor Rotamer Values in ppm in CDCl$_3$)

| Compound | 1 | 7 | 2a | 3a | 5 | 8 |
|---|---|---|---|---|---|---|
| C$_8$ | 164.6, 165.8 | 161.3 | 164.5, 166.1 | 170.8 | 169.7 | 167.0, 165.7 |
| C$_9$ | 196.1, 192.5 | 167.4 | 196.5, 192.0 | 173.1 | — | 192.6, 195.4 |
| C$_{10}$ | 97.0, 98.6 | 89.3 | 97.7, 98.8 | 82.4 | 97.7 | 97.6, 98.1 |

Repetition of the reported degradation protocol (see note 7) of FK-506 gave a methyl ester monoacetate species that was spectroscopically identical to that described by Tanaka and co-workers. However, extensive $^1$H and $^{13}$C NMR investigations support the structure of the degradation product to be the rearranged pyridooxazinedione 7, (see note 6) and not the originally proposed tricarbonyl fragment 6. In addition to the $^{13}$C NMR data shown in the Table, indicating the loss of the C$_9$ ketone with formation of an ester carbonyl, the $^1$H NMR spectrum showed a doublet of doublets at 5.00 ppm (J=6.4, 3.9 Hz) that was unequivocally assigned to 14-H (COSY-45 experiment, see note 8) implying acylation at the C$_{14}$ oxygen, not at the C$_{10}$ oxygen. Two different $^{13}$C 2-D NMR experiments were also performed to verify the position of the acetate moiety on the C$_{14}$ oxygen. A COLOC experiment (see note 9) (Correlation of long range coupling constants) was performed to assign the acetate carbonyl (170.4 ppm), the C$_{10}$ ketone (208.1 ppm), and the methyl ester carbonyl (167.4 ppm). A SELJRES (see note 10) (heteronuclear selective-J-resolved) experiment was then used to establish spin-spin coupling between the C$_{14}$ methine proton and the acetate carbonyl ($^3$J=5.0 Hz), confirming the C$_{14}$ oxygen as acetyl bearing. Evidence for formation of the pyridooxazinedione ring in 7 comes from comparison of $^1$H NMR data for the pipecolinic acid ring protons, in particular 2-H, in 7 versus 1 and 8. In both 1 and 8, 2-H appears as a broad doublet, the only resolved splitting a 4.5 Hz spin-spin coupling to 3-H$_{ax}$, thus defining 2-H as equatorial with C$_1$ axial. in 7, C$_1$ is forced into an equatorial orientation and 2-H is now axial as evidenced by its spin-spin coupling to both C$_3$ methylene protons [$^3$J$_{2,3}$=11.9 Hz (axial, axial), 3.4 Hz (axial, equatorial)]. Further support comes from NOE different experiments on 7 where NOE's are observed between 6-H$_{ax}$ and 2-H (1,3 diaxial orientation). Compound 7 appears to be >85% isomerically pure; however, the stereochemistry at C$_{10}$ is currently unknown.

Further confirmation of the inconsistency of structure 6 with spectral data was gained from examination of synthetic fragment 8 (see note 11). Comparison of the $^{13}$C chemical shifts (see Table) of 8 with 1 and 4 revealed similar chemical shifts for C$_8$, C$_9$ and C$_{10}$. The degradation product, however, exhibits radically different resonances for C$_9$ and C$_{10}$. This comparison removes any doubt that rotamers about the amide bond or the macrocycle itself are responsible for the anomalous chemical shifts observed for the degradation products.

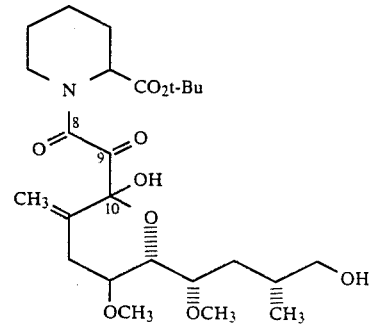

References and Notes

1. Selected IR data for 3b (CHCl$_3$): 1735, 1705, 1640 cm$^{-1}$.
2. Rubin, M. B. *Chem. Rev.*, 1975, 75, p. 177.
3. Rubin, M. B.; Inbar, S. *J. Org. Chem.*, 1988, 53, p. 3355.

4. Pocker, Y.; Davis, B. C. *J. Am. Chem. Soc.*, 1973, 95, p. 6216.
5. Newton, R. F.; Reynolds, D. P.; Finch, M. A. W.; Kelly, D. R.; Roberts, S. M. *Tetrahedron Lett.*, 1979, 20, p. 3981.
6. NMR assignments for 7, $^{13}$C NMR (62.9 MHz, CDCl$_3$): $\delta_C$ 14.9 ($C_{11a}$), 20.3 ($C_{17a}$), 21.0 (OC(=O)CH$_3$), 23.2 ($C_4$), 23.9 ($C_5$), 25.7 ($C_{17}$), 30.1 (O=CCH$_3$), 30.9 ($C_3$), 31.9 ($C_{12}$), 35.5 ($C_{11}$), 36.9 ($C_{16}$), 42.8 ($C_6$), 50.8 ($C_{18}$), 53.7 (ester-OCH$_3$), 56.1 ($C_2$), 56.9, 58.0 (2×OCH$_3$), 74.8 ($C_{14}$), 77.4 ($C_{15}$), 78.2 ($C_{13}$), 89.3 ($C_{10}$), 161.3 ($C_8$), 166.6 ($C_1$), 167.4 ($C_9$), 170.4 (acetate C=O), 208.1 ($C_{19}$).
7. Tanaka, H.; Kuroda, A.; Marusawa, H.; Hatanaka, H.; Kino, T.; Gioto, T. Hashimoto, M.; Taga, T. *J. Am. Chem. Soc.*, 1987, 109, p. 5031.
8. Aue, W. P.; Bartholdi, E.; Ernst, R. R. *J. Chem. Phys.*, 1976, 64, p. 2229.
9. (a) Kessler, H.; Griesinger, C.; Zarbock, J.; Loosli, H. R. *J. Magn. Reson.*, 1984, 57, 331; (b) Kessler, H.; Griesinger, C.; Lautz, J. *Agnew. Chem. Int. Ed. Eng.*, 1984, 23, p. 444.
10. Bax, A.; Freeman, R., *J. Am. Chem. Soc.*, 1982, 104, p. 1099.
11. Compound 8 was synthesized employing standard transformations from compound i (see Askin, D. et al., Tetrahedron Letters 1988, 29, p. 277) via acylation of dithiane ii (see note 12) producing iii. Amide formation and deprotection provided 8. NMR assignments for 8, $^{13}$C NMR (62.9 MHz, CDCl$_3$, major, minor rotameric pairs): $\delta_C$ 16.1, 15.8 ($C_{11a}$), 16.5, 16.7 ($C_{17a}$), 20.7 20.7 ($C_4$), 25.0, 24.3 ($C_5$), 26.2, 27.6 ($C_3$), 27.9 (C(CH$_3$)$_3$), 32.0, 32.3 ($C_{16}$), 32.4, 32.0 ($C_{17}$), 32.8, 32.3 ($C_{12}$), 33.5, 34.3 ($C_{11}$), 44.6, 39.2 ($C_6$), 52.1, 56.9 ($C_2$), 56.2, 56.0 (OCH$_3$), 57.4, 57.5 (OCH$_3$), 68.6, 68.5 ($C_{18}$), 72.1, 73.0 ($C_{14}$), 73.5, 73.6 ($C_{13}$), 75.6, 75.5 ($C_{15}$), 83.3, 82.7 (OC(CH$_3$)$_3$), 97.6, 98.1 ($C_{10}$), 167.0, 165.7 ($C_8$), 168.8, 170.0 ($C_1$), 192.6, 195.4 ($C_9$).

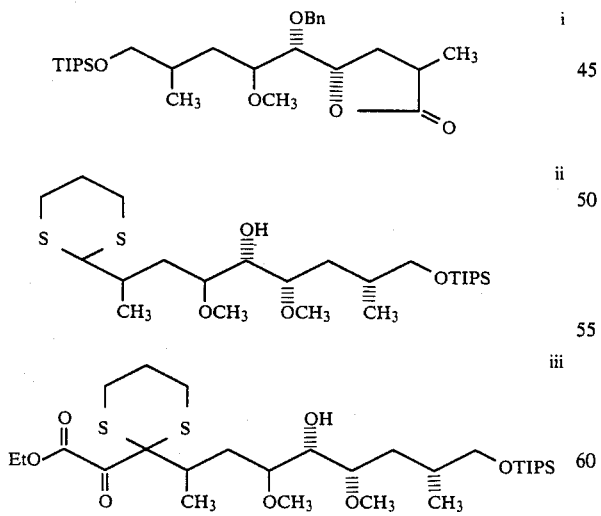

12. Corey, E. J.; Hua, D. H.; Pan, B. C.; Seitz, S. P. *J. Am. Chem. Soc.*, 1982, 104, p. 6818.

What is claimed is:
1. A process comprising the steps of:
(a) contacting compound 2:

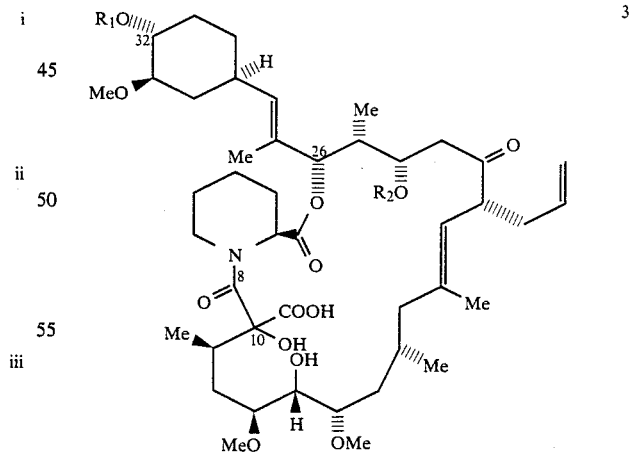

wherein $R_1$ and $R_2$ are independently H, or an easily removable hydroxy protecting group, with a hydroxide base in an inert aqueous/organic solvent mixture at room temperature in the range of about 0°–25° C. for a sufficient time to form 3;

(b) contacting 3 obtained above with an oxidizing agent in an inert organic solvent at 0°–50° C. for a sufficient time to form 4;

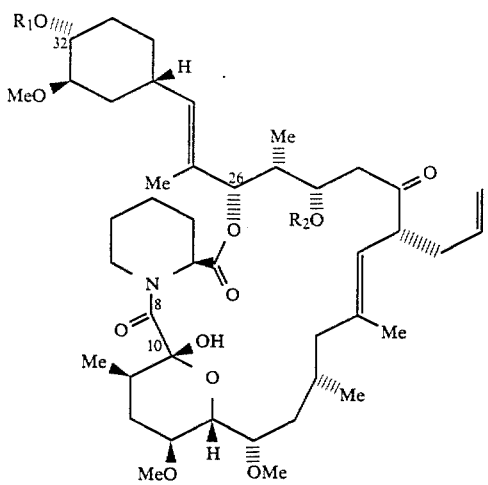

(c) contacting the above-obtained 4 under mild acidic hydrolysis conditions for a sufficient time to remove $R_2$ and/or $R_1$ if either are present, to yield the immunosuppressant 5:

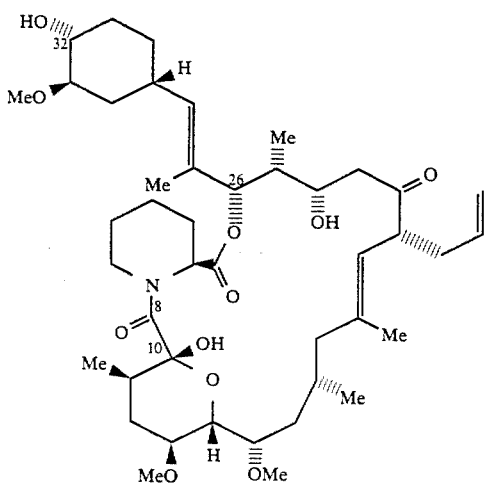

2. The process of claim 1 wherein $R_1$ and $R_2$ are independently selected from radicals easily hydrolyzable under mild acid conditions selected from $C_1$-$C_{10}$ acyl or halogenated $C_1$-$C_{10}$ acyl; $C_1$-$C_{10}$ halogenated alkyl; $SiR_3$, where R is independently $C_1$-$C_4$ linear or branched alkyl, phenyl, or benzyl.

3. The process of claim 2 wherein said $R_1$ and $R_2$ are both triisopropylsilyl.

4. The process of claim 2, step (a), wherein said hydroxide base is of the formula: $M(OH)_n$, where M is Na, K, Cs, Li, Mg, Ca, Ba and n is 1 or 2.

5. The process of claim 4 wherein said hydroxide base is LiOH.

6. The process of claim 1, step (a), wherein said organic solvent is a $C_1$-$C_{10}$ cyclic or acyclic ether.

7. The process of claim 1, step (b), wherein said oxidizing agent is lead tetraacetate or an alkali metaperiodate.

8. The process of claim 1, step (a), conducted in the temperature range of 0°–5° C.

9. The process of claim 1, step (b), conducted in the temperature range of 20°–25° C.

10. A process comprising the steps of:

(a) contacting compound 2a, wherein "TIPS" is triisopropylsilyl:

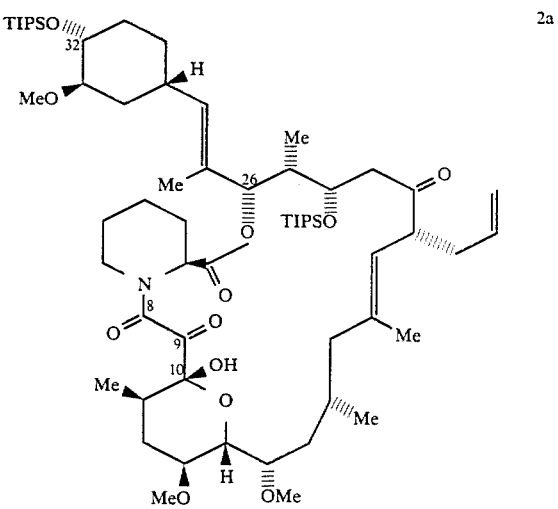

with lithium hydroxide in aqueous tetrahydrofuran at 0°–5° C. for a sufficient time to form 3a;

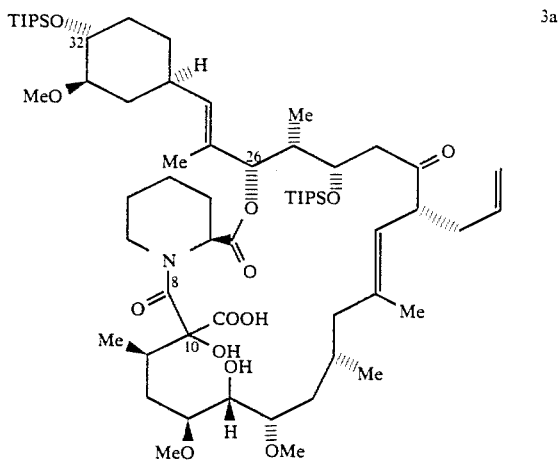

(b) contacting 3a obtained above with lead tetraacetate in dry benzene at 20°–25° C. for a sufficient time to form 4a;

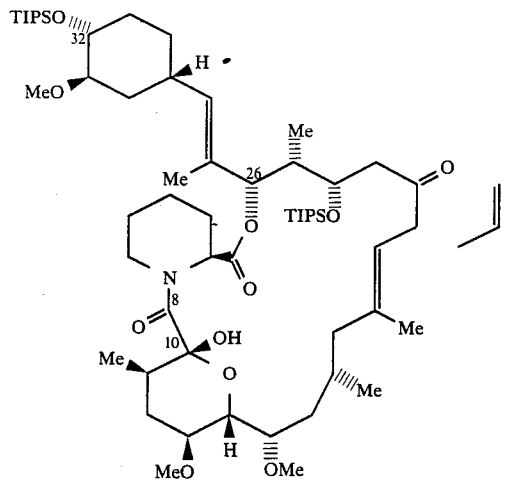
(c) contacting the above-obtained 4a with aqueous HF in acetonitrile at 20°–25° C. for a sufficient time to remove the triisopropylsilyl protecting groups, to yield the immunosuppressant 5:
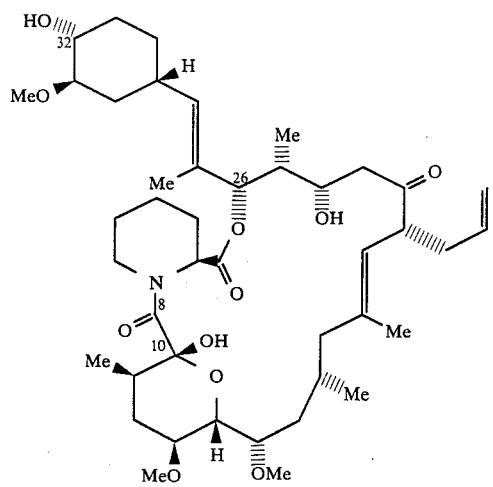
* * * * *